United States Patent [19]

Karol et al.

[11] 4,383,984
[45] * May 17, 1983

[54] TOLYL ISOCYANATE AND TOLUENE DIISOCYANATE TEST ANTIGENS, METHODS FOR THEIR PREPARATION AND USE IN DETECTING DIISOCYANATES AND ANTIBODIES TO DIISOCYANATES

[75] Inventors: Meryl H. Karol; Yves C. Alarie, both of Pittsburgh, Pa.

[73] Assignee: University of Pittsburgh, Pittsburgh, Pa.

[ * ] Notice: The portion of the term of this patent subsequent to Jun. 17, 1997, has been disclaimed.

[21] Appl. No.: 159,582

[22] Filed: Jun. 16, 1980

Related U.S. Application Data

[63] Continuation-in-part of Ser. No. 934,023, Aug. 16, 1978, Pat. No. 4,208,399.

[51] Int. Cl.$^3$ ..................... G01N 33/58; G01N 33/60
[52] U.S. Cl. .................................. 424/1; 260/112 B; 436/573; 436/543
[58] Field of Search ................ 424/1, 12; 23/230 B; 260/112 B

[56] References Cited

U.S. PATENT DOCUMENTS

| | | | |
|---|---|---|---|
| 3,443,903 | 5/1969 | Haack | 23/230 B |
| 3,549,328 | 12/1970 | Kilburn | 23/230 B |
| 3,838,012 | 9/1974 | Higgins | 23/230 B |
| 4,031,197 | 6/1977 | Maunkovich | 424/1 |
| 4,208,399 | 6/1980 | Karol et al. | 424/1 |
| 4,243,651 | 1/1981 | Nalebuff | 424/1 |

*Primary Examiner*—Christine M. Nucker
*Attorney, Agent, or Firm*—Buell, Blenko, Ziesenheim & Beck

[57] ABSTRACT

An antigen and a method for its preparation and use in detecting antibody to a selected diisocyanate is provided by reacting the monoisocyanate derivative of the diisocyanate or the diisocyanate with a protein, incubating the antigen on a paper disc with test serum in the presence of a buffer and anti-IgE-$^{125}$I and thereafter counting the disc with a scintillation spectrometer.

4 Claims, 5 Drawing Figures

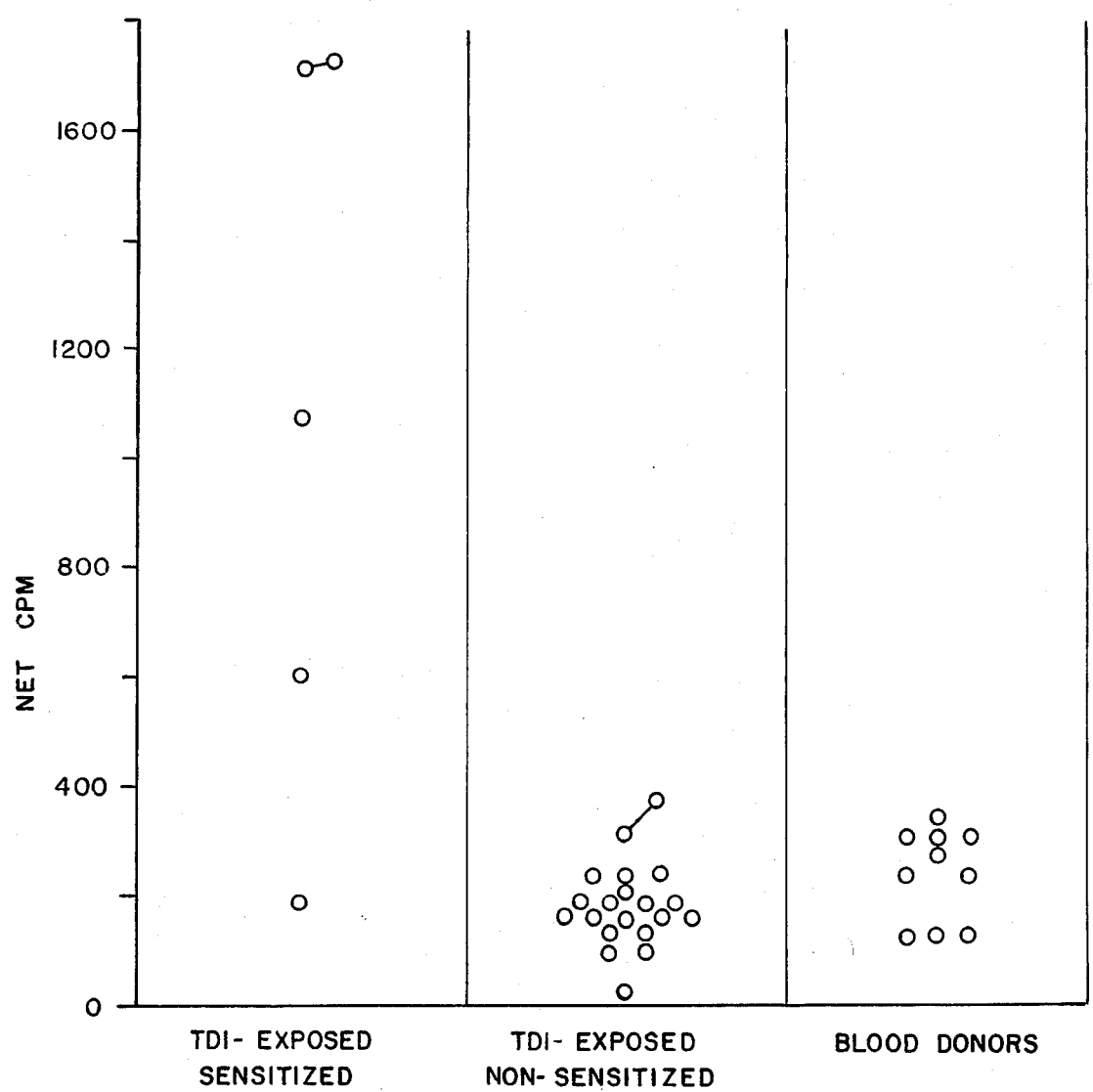
FIGURE 1 — RAST assay for tolyl-specific IgE in sera from workers exposed to TDI and from Blood donors. Connected points indicate titers of sera taken one month apart from the same individual. Net cpm = cpm (TMI-HSA discs) − cpm (HSA discs).

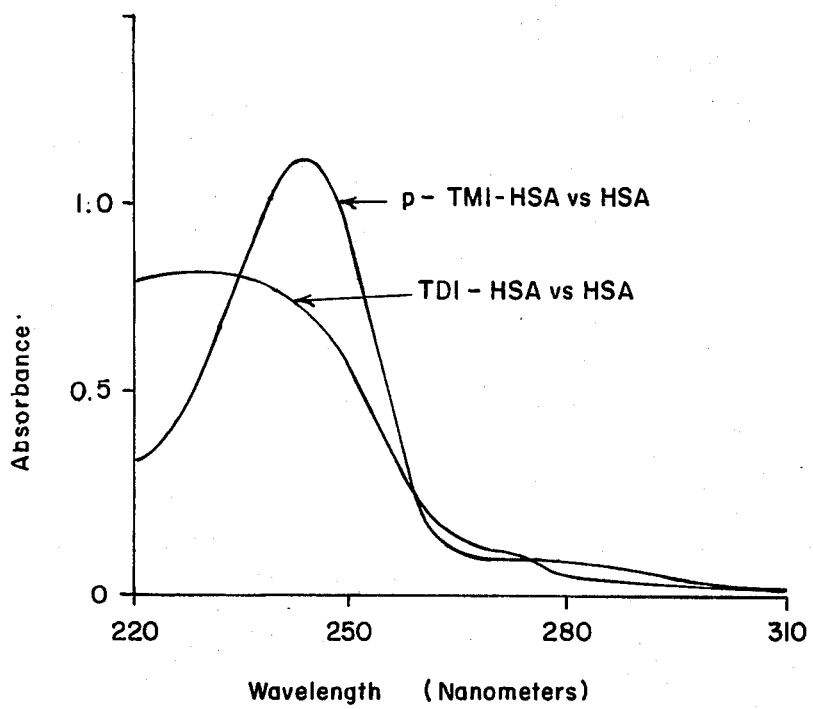
FIGURE 2 — Ultraviolet absorption difference spectra. Human serum albumin (HSA), p-tolyl(mono)isocyanate-human serum albumin (p-TMI-HSA) and toluene diisocyanate-human serum albumin (TDI-HSA) each at 125 μg per ml 0.05 M phosphate buffer pH 7.0. The difference spectra of p-TMI-HSA versus HSA and TDI-HSA versus HSA.

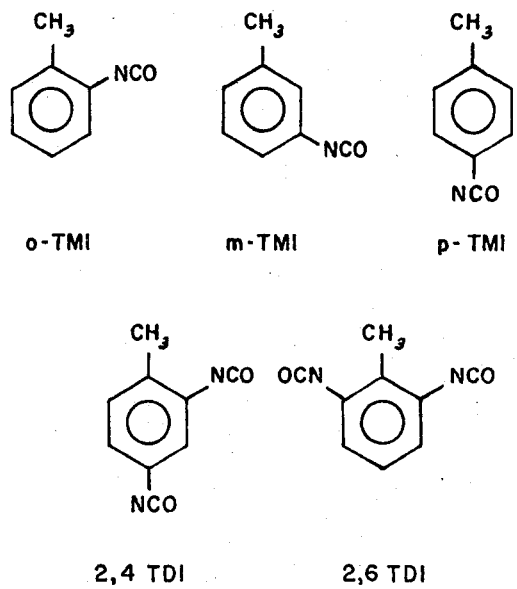
FIGURE 3 — Haptens used in antigen preparations. o-TMI, ortho-tolyl isocyanate; m-TMI, meta-tolyl isocyanate; p-TMI, para tolyl isocyanate; 2,4 TDI, 2,6 TDI, isomers of toluene diisocyanate (80/20 mixture).

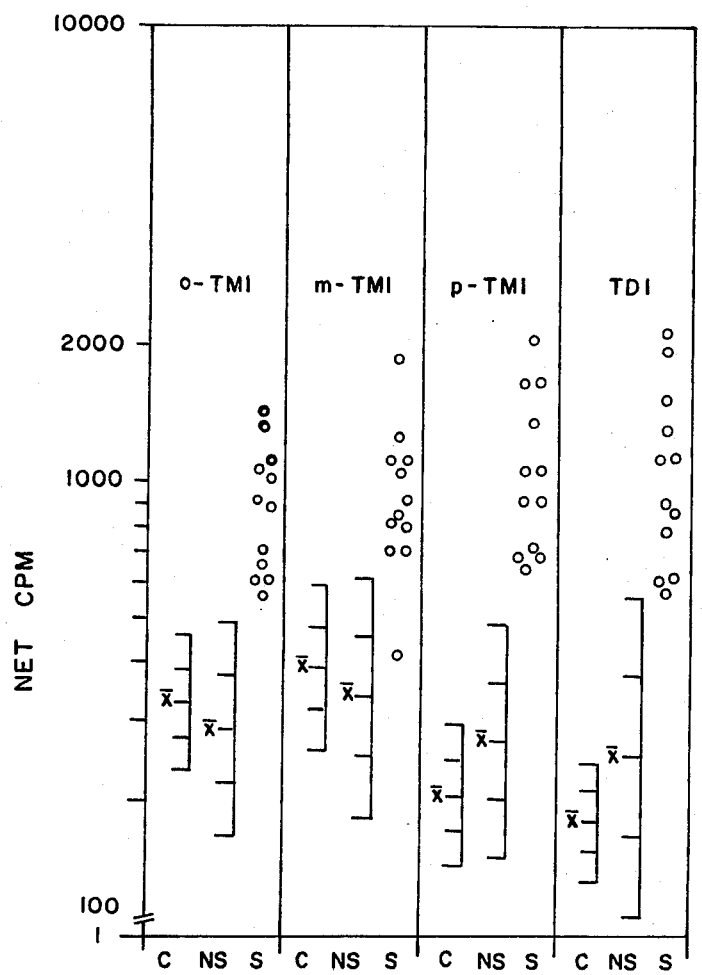

FIGURE 5 — RAST assays for tolyl-reactive IgE antibodies. Antigens: o-TMI, ortho-tolyl isocyanate-human serum albumin; m-TMI, meta-tolyl isocyanate-human serum albumin; p-TMI, para-tolyl isocyanate-human serum albumin; TDI, toluene diisocyanate-human serum albumin. Sera: C, cord sera (n=25); NS, non-sensitive workers (n=25); S, TDI-sensitive workers (n=12). Net cpm = cpm ("tolyl"-HSA discs) − cpm (HSA discs). Bars indicated geometric mean ($\bar{X}$) and 1 and 2 $\sigma_g$.

TOLYL ISOCYANATE AND TOLUENE DIISOCYANATE TEST ANTIGENS, METHODS FOR THEIR PREPARATION AND USE IN DETECTING DIISOCYANATES AND ANTIBODIES TO DIISOCYANATES

This invention resulted from work done under Contract No. ROI-ES01532 with the National Institute of Environmental Health Science of the Department of Health, Education and Welfare, and is subject to the terms and conditions of the Presidents Patent Policy Statement of Oct. 10, 1963.

This application is a continuation-in-part of our co-pending application, Ser. No. 934,023, filed Aug. 16, 1978, now U.S. Pat. No. 4,208,399.

This invention relates to tolyl isocyanate test antigens, methods for their preparation and use in detecting diisocyanates and antibodies to diisocyanates and particularly to a tolyl isocyanate test antigen for the detection of hypersensitivity antibodies to toluene diisocyanate and other diisocyanates in workers.

Diisocyanates and particularly toluene diisocyanate (TDI) are highly reactive chemicals used in the manufacture of plastics, foams and paints. They are the basic ingredients in the group of plastics known as urethanes which are used in the manufacture of insulation cushioning material, building panels, food containers and a vast array of goods. TDI in particular has been cited frequently as a potent sensitizer in the industrial environment, possibly because it is such a heavily used item. However, other industrial diisocyanates such as hexamethylene diisocyanate, diphenyl methane diisocyanate, isophorone diisocyanate and naphthylene diisocyanate find substantial use in industry and pose a like problem of hypersensitivity. It is generally recognized that about 5% of those persons exposed to TDI become sensitized and suffer asthmatic reactions upon subsequent exposure to even extremely low concentrations of the chemical. A great deal of work has been done in an effort to find a specific test for the presence of this sensitivity and specifically for TDI specific antibodies through which some measure of sensitivity might be established. This past work has failed to produce any satisfactory test or machanism for detecting anti-TDI antibodies. The difficulty in detecting anti-TDI antibodies may result from the chemical reactivity of TDI. The known tendency of TDI to cross-link protein molecules apparently precludes preparation of hapten-conjugated test antigens which contain exposed tolyl groups. In any event a satisfactory test technique has evaded prior attempts at solution.

We have discovered that test antigens for TDI can be prepared from the monoisocyanate derivatives of toluene and from TDI itself. Similarly test antigens of other industrial diisocyanates can be prepared from the corresponding monoisocyanate analogues and these monoisocyanate analogues are suitable for detecting the diisocyanates and antibodies thereof. Since the TDI detection is by far the most important due to the large tonnages of TDI used in industry and the corresponding greater exposure we shall illustrate the preparation of monoisocyanate antigen and use of TDI for preparation of satisfactory test antigens for induction of tolyl specific serum antibodies in mammals.

The invention can accordingly be best understood from the test examples set out hereafter and from the drawings in which:

FIG. 1 is a graph of RAST radioimmunoassay for a group of test sera;

FIG. 2 is a graph of ultraviolet absorption difference spectra;

FIG. 3 is a schematic illustration of the hapten used;

FIG. 4 is a double diffusion in agarose of three TDI sensitized guinea pigs; and FIG. 5 is a comparison of RAST assays for tolyl-reactive IgE antibodies.

Test Subjects

Twenty-three employees of a large TDI production facility were chosen as test subjects. At the time of this test all subjects had been employed at TDI production facility for at least one year. Four of the employees were considered to be sensitive to TDI; three of these four had experienced a hypersensitivity response (either pulmonary or cutaneous) within one year prior to the study, the fourth individual had take precaution to avoid exposure to TDI for at least two years prior to study. The remaining nineteen employees were not considered to be sensitive to TDI. This conclusion was based on inhalation challenge studies using 0.02 ppm TDI or complete absence of adverse reactions upon TDI exposure. Sera were evaluated using a blind study. Identities of the donors were made known only after completion of all serological determinations. The study also included sera from ten adult healthy blood bank donors.

The test thus involved twenty-three persons employed at a TDI facility and ten randomly selected persons for a total of thirty-three subjects.

The Test Antigen

A test antigen containing p-tolyl isocyanate and human serum albumin (HSA) was prepared as follows: 280 μl p-tolyl isocyanate (Eastman Organic Chemicals) was added to a chilled, rapidly stirred, 1% solution of HSA (Sigma Chemical Co.) in borate buffer at pH 9.4. Following extensive dialysis, spectroscopic examination of the conjugate indicated an average substitution of ten moles of hapten per mole HSA. This antigen formulation follows the pattern:

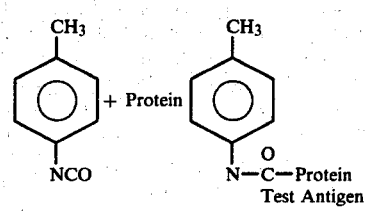

The corresponding formulations for antigens of the monoisocyanate analogues of other industrial diisocyanates is typified by the following equations:

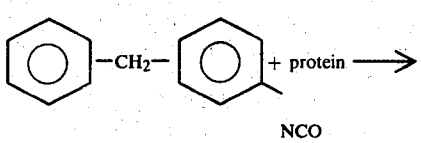

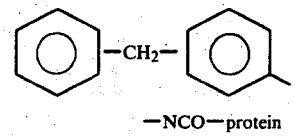

diphenyl-methane-4-isocyanate

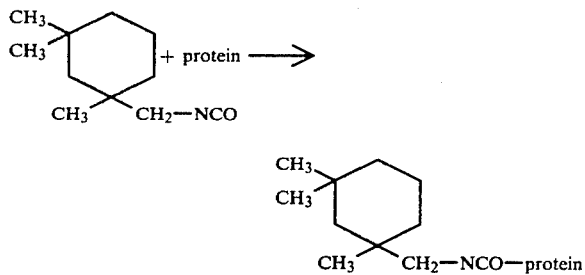

isophoronisocyanate

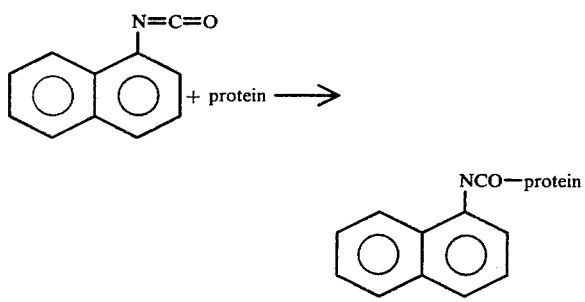

naphthylene isocyanate

Radioimmunoassay for anti-tolyl antibodies

A RAST (Radioallergosorbent Test) was developed using the TMI-HSA antigen bound to 5 mm paper discs (Whatman #44), the latter previously activated with cyanogen bromide. For coupling, 4 ml antigen (20 mg/ml) in 0.1 M NaHCO$_3$ was added to 100 mg activated discs and the mixture was incubated on a rotator at ambient temperature for 6 hours. Discs were then washed 3 times with 0.1 M monoethanolamine in 0.1 M NaHCO$_3$ and stored in this solution overnight at 10° C. The following day, discs were washed 3 times with incubation buffer (0.05 M phosphate, pH 7.4, 0.85% NaCl, 1.0% bovine serum albumin, 0.05% NaN$_3$). For the test, 100 μl serum was added to a tube containing an antigen-coated disc and incubated overnight on a rotator at ambient temperature. Discs were then washed 3 times with 0.85% NaCl-1% Tween 20 (S-T) before incubation with 100 μl anti-IgE $^{125}$I (Phadebas Rast reagent, Pharmacia Diagnostics 1977). The latter reagent is specific for the D$\epsilon_2$ determinant of human IgE. Following overnight incubation, discs were again washed 3 times with S-T then counted in 10 ml ACS scintillation fluid (Amersham Searle Corporation) using the tritium channel on a Packard Tri-Carb liquid scintillation spectrometer. All sera were processed in duplicate. IgE antibody reactive with tolyl groups was determined from the activity bound to TMI-HSA-coated discs compared with activity bound to HSA-coated discs. The latter values were obtained from separate incubation of serum samples with paper discs reacted with HSA alone. The correction ranged between 100-150 counts per minute. Tolyl-specificity of IgE antibodies was also indicated by hapten inhibition studies as detailed below.

Hapten inhibition of serum binding

Tolyl-specificity of IgE antibody binding to TMI-HSA paper discs was additionally measured by hapten inhibition. Haptens used were toluene 2,4 diamine and a conjugate of p-tolyl isocyanate and ε-aminocaproic acid. Synthesis of the conjugate hapten was carried out by dropwise addition of p-tolyl isocyanate and ε-aminocaproic acid to a chilled 1% solution (w/v) of ovalbumin (Sigma, Grade V) in 0.05 M boric acid-0.05 M KCl-0.035 M NaOH buffer, pH 9.4. The synthesis employed equimolar amounts of the two reactants. The reaction mixture was stirred at 0° C. for 30 minutes and then centrifuged. The supernatant was allowed to react an additional 60 minutes, then dialyzed against saline for 24 hours, then against distilled water for 72 hours. The product was isolated by acidification of the reaction mixture to pH 4.5. Following purification of p-tolylureido caproate by repeated acid-base precipitation and dissolution, it was recrystallized from hot ethanol $\epsilon_{242nm}=11,440$, mp=135° C. The extent of "tolyl" substitution of tolyl ovalbumin was determined from the 242 mn absorbance in excess of that due to ovalbumin. To demonstrate inhibition, TMI-HSA coated discs were incubated with test serum (100 μl) in the presence of hapten dissolved in 50 μl normal horse serum (Pharmacia Diagnostics). Following a 24 hour incubation, IgE binding to the discs was evaluated using anti-IgE-$^{125}$I as described above. Inhibition was determined by comparison of the binding of the test serum in the presence and absence of inhibitor.

Total IgE

The Phadebas IgE PRIST test kit (Pharmacia Diagnostics) was used to determine total IgE in sera. Values were converted to IgE Units/ml by comparison with a standard serum supplied by the manufacturer.

RESULTS

Tolyl-specific IgE

Results of the RAST radioimmunoassay for IgE antibody bound to TMI-HSA discs are presented as net counts per minute (cpm) in FIG. 1 and Table I. The group of 19 TDI-exposed, non-sensitized workers had antibody titers comparable to those found in sera from blood bank donors. The TDI-sensitized group, on the other hand, displayed markedly elevated titers of anti-tolyl antibody. The geometric mean titer of the latter group of sera differed significantly from that of the non-sensitized workers (99% confidence level, t test with unequal variance). Within the TDI-sensitized group, the only serum lacking a significant antibody titer (P<0.05) was from the individual unexposed to TDI for at least two years prior to study. Each of the other three TDI-sensitive persons had significant titers. In two cases, it was possible to obtain second serum samples one month following the initial sample. The first and second determinations from individual workers are indicated with a connecting line in the Figure.

Tolyl-specificity of IgE binding to TMI-HSA discs was demonstrated by hapten inhibition. In the presence of 500 μg p-tolyl ureido caproate in one case, and 250 μg toluene 2,4 diamine in another case, 50% and 48% less antibody became bound to the TMI-HSA discs, respectively. The same quantities of hapten had no inhibitory effect in control IgE-anti-IgE$^{125}$I PRIST systems.

Total IgE Concentrations

To determine if the tolyl-reactive IgE antibodies identified in sera from TDI-sensitized persons merely reflected high levels of IgE in the serum, total serum IgE was measured. The results, shown in Table I, indicate no apparent relationship between tolyl-directed IgE antibodies and the amount of IgE in sera. Cases #1,

4 and #15, each with significant titers of tolyl-specific IgE antibody, did not have unusually high amounts of total IgE. Moreover, the elevated levels of IgE seen in cases #3, #6 and #8, did not correlate with increased levels of tolyl-specific IgE antibody.

TABLE I

Total IgE and Tolyl-Specific IgE in Workers Exposed to Toluene Diisocyanate (TDI)

| Case | Total IgE* (Units/ml) | Tolyl-Specific IgE (net cpm) |
|---|---|---|
| +1 | 42 | 1714 |
| 2 | 71 | 154 |
| 3 | 90 | 247 |
| +4 | 36 | 598 |
| 5 | 25 | 179 |
| 6 | >100 | 311 |
| 7 | 22 | 150 |
| 8 | 95 | 240 |
| 9 | <1 | 115 |
| 10 | 9 | 160 |
| 11 | 84 | 230 |
| 12 | 3 | 151 |
| 13 | 84 | 128 |
| 14 | 34 | 195 |
| +15 | 10 | 1077 |
| 16 | 65 | 18 |
| 17 | 44 | 82 |
| 18 | 4 | 99 |
| 19 | 54 | 142 |
| 20 | 82 | 210 |
| +++21 | 56 | 187 |
| 22 | 11 | 199 |
| 23 | 86 | 173 |

*Geometric mean value for normal adults is 14 Units/ml.
+ Workers with clinical evidence of sensitivity to TDI.
++ Worker unexposed to TDI for >2 years prior to this study.

The foregoing test results are directed toward identification of the IgE class of antibody in workers displaying clinical TDI hypersensitivity. The titers of tolyl-IgE antibody found in sera from TDI-exposed, non-sensitive workers were indistinguishable from antibody levels found in the normal adult population studied. It is apparent, therefore, that the presence of tolyl-specific IgE antibodies is not solely a reflection of TDI exposure. The occurrence of specific IgE antibodies only in those workers with hypersensitivity to the isocyanate implies a causal role for these antibodies.

Tolyl-specific IgE antibodies were detected in three of the four sensitized workers. The highest titer (case #1) was found in a person with acute pulmonary hypersensitivity to TDI. This person responded to bronchial challenge with 0.006 ppm TDI. Cases #4 and #15 display immediate skin reactions upon exposure to TDI. This skin sensitivity was not of the irritant type since the affected areas were extensive and not confined to regions where TDI contacts the skin. Allergic eczema to TDI has been reported although most reports of TDI hypersensitivity pertain to the bronchial response. The fourth case (#21) of TDI-hypersensitivity had not been exposed to TDI for at least two years prior to this study. Failure to detect tolyl-specific antibodies in this instance may reflect the rapid turnover of serum IgE.

Further research has shown test antigens prepared from proteins and tolyl monoisocyanate isomers as haptens as well as TDI hapten have the ability to detect anti-TDI antibodies. The mechanisms and tests employed are set out hereafter.

METHODS

Antigens

Conjugate antigens were prepared by coupling several tolyl monoisocyanates (Eastman Chemicals) or toluene diisocyanate (Mondur TD-80, 80/20 mixture 2,4 and 2,6 isomers; Mobay Chemical Corp.) to human serum albumin (HSA) or guinea pig serum albumin (GSA) according to a published procedure (Am. Inst. Hyg. Assoc. J. 39 [1978] 546-556). Briefly, the method consisted of dropwise addition of isocyanate to a stirred 1% solution of serum albumin maintained in buffer, at pH 9.4. Reaction time was varied from one to three hours to achieve an average binding of 30-40 moles hapten per mole protein. Conjugates were isolated by lyophilization following extensive dialysis. The following conjugate antigens were prepared: o-tolyl isocyanate-human serum albumin (o-TMI-HSA), m-tolyl isocyanate-human serum albumin (m-TMI-HSA), p-tolyl isocyanate-human serum albumin (p-TMI-HSA) and toluene diisocyanate-human serum albumin (TDI-HSA). The extent of haptenic substitution of protein by monoisocyanate was determined by spectrophotometric analysis. Each of the monoisocyanate-protein conjugates displayed a narrow ultraviolet absorption peak when analyzed versus serum albumin (see FIG. 2). Similar analysis of TDI-HSA revealed a broad peak of absorbance in the ultraviolet region as indicated in FIG. 2. Because of the multitude of haptenic reaction products, quantitative assessment of diisocyanate binding was not made.

Immunization of guinea pigs

Female, English smooth-haired guinea pigs (Hilltop Lab Animals, Scottdale, PA) were exposed to TDI according to one of the following procedures: A. Inhalation route. Four sets of guinea pigs, containing four animals per set, were exposed to 0.25 ppm TDI using head only exposures. TDI vapor was generated by bubbling dried air through TDI contained in a glass impinger. The TDI vapor was directed into a 10 liter Plexiglass inhalation chamber. Air was drawn through the chamber at a rate of 20 liters/minutes. Analytical determination of TDI concentration in the chamber was made using the method of Marcali (anal. Chem. 1957; 29: 552-58) as modified by NIOSH (Mannal of Analytical Methods, 2nd Ed. Vol., pp 141.1, 141.8) B. Dermal route. Four guinea pigs were sensitized by application of 100 μl TDI to a site on the shaved dorsal area. Animals were bled 14 days later. C. Injection. Four guinea pigs received an intraperitoneal injection of 100 μl TDI. Fourteen days later, animals were bled for serologic study.

Human sera

TDI-sensitive workers. Antibody measurements were performed on sera from twelve industrial workers which had been submitted to this laboratory for TDI antibody determination. These workers were diagnosed by their Medical Directors as clinically sensitive to TDI.

TDI-nonsensitive workers. Serum was obtained from twenty-five persons, each of whom had been employed in TDI manufacture for at least one year. None of these persons had evidence of sensitivity to TDI, either pulmonary or cutaneous.

Cord blood. Twenty-five cord sera were obtained.

Antibody analysis

RAST. For RAST assays, antigens were coupled to cyanogen bromide-activated discs. For the assays, 50 μl of the subject's serum were added to antigen-coated discs. Following incubation of discs with serum at ambient temperature for 16 hours, discs were washed thoroughly with 0.85% saline-1.0% Tween 20 solution.

Fifty microliters of I$^{125}$-labeled rabbit anti-human IgE (specific for the D$\epsilon_2$ region; RAST reagent, Pharmacia Diagnostics) were added, and the discs incubated at room temperature for an additional 16 hours. Following thorough washing, radioactivity bound to discs was determined using a Packard liquid scintillation spectrometer. All tests were performed in a blind manner. Determinations were performed a minimum of two times. Replicates differed by less than 10%.

Immunodiffusion. The double diffusion technique was used to evaluate antibody reactivity of guinea pig sera. Microscope slides (75×50 mm) were coated with 6 ml 1% agarose (Biorad) in 0.1 M borate-borax, pH 8.4. Antisera were placed in central wells (3 mm D) and antigens added to peripheral wells (2 mm D). Where indicated, antisera were concentrated using Minicon concentrators (Amicon Corp.). Diffusion was permitted for 48 hours in a closed vessel at ambient temperature. Gels were then placed in a solution of 5% trisodium citrate for 24 hours for removal of possible non-specific (non-immunologic) precipitates.

RESULTS

Guinea pig anti-TDI antibodies

Antibodies to TDI were produced in guinea pigs following exposure by inhalation, dermal content or intraperitoneal injection. Antibody specificity was determined by testing sera for reactivity with several related tolyl haptens. Structures of these haptens are shown in FIG. 3. Wide differences in antibody reactivity were noted among individual guinea pigs. In certain animals, antibodies reacted only with the TDI-conjugate antigen; in others, reactions were noted with each of the three tolyl monoisocyanate antigens as well. Findings representative of the range of responses seen are presented in FIG. 4. The serum in FIG. 4A reacted extensively with TDI-GSA and to a lesser extent with p-TMI-GSA. No bands were apparent with the ortho-tolyl antigen or the meta-tolyl antigen. In comparison, the serum shown in FIG. 4A gave strong reactions with TDI-GSA, o-TMI-GSA p-TMI-GSA. A weaker reaction was noted with m-TMI-GSA. A third serum (FIG. 4C) reacted best with TDI-GSA, to a lesser extent with o-TMI-GSA, p-TMI-GSA and m-TMI-GSA and showed clear "spur" formation in reaction between TDI-GSA and o-TMI-GSA. The latter finding indicates antigenic determinants in TDI-GSA which are not present in o-TMI-GSA. In no instance was precipitation observed with GSA. Sera from the same animals taken prior to TDI exposure were always negative in these assays.

Antibodies in human sera

Sera from twelve TDI-sensitive and twenty-five non-sensitive workers were evaluated for IgE antibody reactive with each of the tolyl conjugated antigens. Results of the RAST assays are presented in FIG. 5. Each of the hapten-conjugate test antigens detected antibodies in sera from sensitive (S) workers. Significant antibody titers, values greater than the geometric mean +2 $\sigma$g of the non-sensitive (NS) control group, were present in eleven of twelve experimental sera using any of the four RAST antigens. All but the m-TMI-HSA RAST additionally detected antibodies in the remaining sensitive sample. Sera with highly significant antibody titers in one assay usually gave highest values in other RAST assays. In no case did a serum react only in the TDI-HSA RAST.

Sera from TDI-exposed non-sensitive (NS) workers had titers of 100–600 net cpm in each of the RAST assays. Geometric mean values (+1, 2 $\sigma$g) for this group are indicated in FIG. 4. To determine if this level of net tolyl reactivity represented specific antibody, or alternatively, if it reflected non-specific binding to discs, RAST was performed using twenty-five neonatal (cord) sera. Since cord sera contain extremely low levels of total IgE (11) finding cpm in cord sera equivalent to those in sera of non-sensitive workers would indicate non-specific binding in tolyl RAST assays. As seen in FIG. 4, cpm in cord sera and sera from non-sensitive workers were comparable, although the variance of cord sera was smaller in all assays. These results indicated that tolyl-specific IgE antibodies were not present in sera from non-sensitive workers.

The guinea pig model for TDI sensitivity was employed here to investigate the reactivity of anti-TDI antibodies toward several tolyl (mono) isocyanate conjugate antigens. It was anticipated that evaluation of these antibodies would indicate which antigens would be most effective in detecting anti-TDI antibodies in man. Gel diffusion analysis was used to evaluate animal antisera. This technique was selected because it offers visual presentation of cross-reactions between related antigen-antibody systems while using minimal amounts of sera.

Guinea pigs sensitized by any of the three described routes produced antibodies to TDI. However, considerable differences existed between animals within each group regarding antibody titers and specificity. Antibodies generally reacted to a greater extent with the TDI conjugate than with any of the monoisocyanate hapten conjugates. This conclusion was based on: (a) precipitation of some antisera with TDI-GSA and absence of precipitin bands with monoisocyanate conjugates and (b) spur formation. In addition, quantitative antibody determinations using the passive cutaneous anaphylaxis (PCA) technique, revealed highest titers with the TDI-conjugate antigen (data not shown here). Many of the sensitized guinea pigs produced antibodies cross-reactive with ortho, para and meta tolyl isocyanate antigens. In these cases, reactions were usually weakest with the meta-tolyl conjugate (see FIG. 4).

For evaluation of human sera, the RAST procedure was used. This technique was selected because it enabled detection of IgE antibodies, the immunoglobulin class most frequently associated with immediate hypersensitivity responses in man. Sera from TDI-sensitive workers displayed antibodies reactive with the TDI-conjugate and, in eleven of twelve cases, with each of the monoisocyanate test antigens. In these assays, as in the guinea pig system, antibodies reacted with the meta tolyl hapten. Cross-reaction of anti-TDI sera with meta-tolyl determinants was not unexpected even though TDI is composed exclusively of ortho and para-positioned isocyanate groups. The serologic reactions observed with m-tolyl antigens would be typical of antibody cross-reactions. As early as 1906, for instance, Landsteiner recognized that anti-sera produced to p-toluidine cross-reacted with both o-toluidine and m-toluidine haptens.

RAST testing of large numbers of workers for TDI antibodies requires standardization of antigen preparations. The complex reactions of TDI make uniform preparations of antigen difficult. In order to achieve a degree of uniformity, monofunctional tolyl isocyanate haptens were used for antigen synthesis and tested for ability to react with anti-TDI antibodies produced in guinea pigs and in man. The results of this study indicate that ortho, meta and para-tolyl monoisocyanate haptens react with antibodies produced to TDI. In the guinea pig system, the TDI-conjugate was usually superior to monoisocyanate antigens in detecting antibodies. In the RAST assays of human sera however, little difference was observed between the TDI-conjugate and the monoisocyanate antigens in detecting anti-TDI antibodies.

Use of a toluene monoisocyanate-human serum albumin test antigen as in this invention has permitted detection of tolyl-specific antibodies in TDI-sensitized workers. This finding supports an immunologic pathogenesis of TDI hypersensitivity. It is anticipated that this antigen will prove useful both in serological assays and in cutaneous testing for identification of sensitized individuals. By their removal from the exposure environment, it may be possible to prevent cutaneous or bronchial hypersensitivity reactions to TDI. In any event, the antigen and test method here disclosed makes it possible for the first time effectively to determine those persons who are sensitive to TDI.

In the foregoing specification we have set out certain preferred practices and embodiments of our invention, however, it will be understood that this invention may be otherwise practiced within the scope of the following claims.

We claim:

1. An antigen for detection of a selected diisocyanate comprising the reaction product of a protein and the particular select diisocyanate or the monoisocyanate analogue of the select diisocyanate.

2. An antigen as claimed in claim 1 wherein the protein is human serum albumin.

3. A serological diagnostic test for a selected diisocyanate comprising the steps of:
    (a) preparing an antigen of said selected diisocyanate by reacting a protein with toluene diisocyanate;
    (b) adding said antigen to a paper disc activated with a coupling agent;
    (c) buffering said disc with an incubation buffer;
    (d) adding serum from a test subject to said buffered disc;
    (e) incubating said serum and disc with anti-IgE-$^{125}$I; and
    (f) counting said disc in scintillation fluid using a scintillation spectrometer.

4. A serological diagnostic test as claimed in claim 3 wherein the protein is human serum albumin.

* * * * *

UNITED STATES PATENT AND TRADEMARK OFFICE
CERTIFICATE OF CORRECTION

PATENT NO. : 4,383,984

DATED : May 17, 1983

INVENTOR(S) : MERYL H. KAROL and YVES C. ALARIE

It is certified that error appears in the above-identified patent and that said Letters Patent is hereby corrected as shown below:

Add Fig. 4 of the drawings as shown on the attached page.

Signed and Sealed this

Twenty-first Day of August, 1990

Attest:

HARRY F. MANBECK, JR.

*Attesting Officer*        *Commissioner of Patents and Trademarks*

FIG. 4A

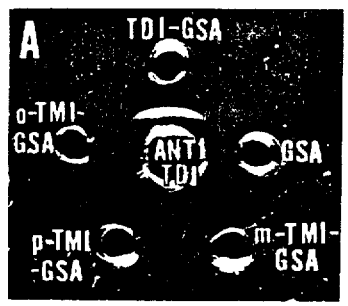

FIG. 4B

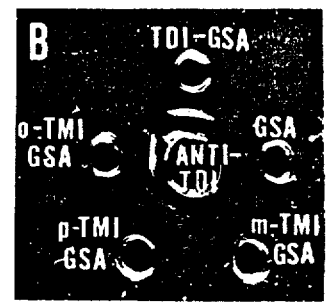

FIG. 4C

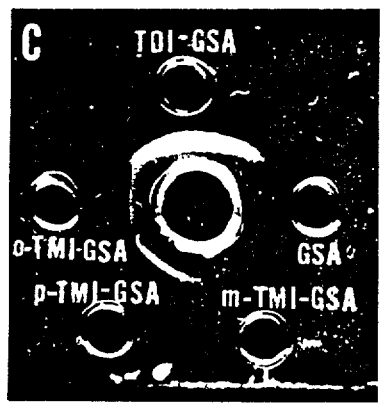

FIG. 4

Double diffusion in agarose of sera from three individual guinea pigs sensitized to TDI. Sera were concentrated five-fold and placed in central wells. Antigens (each 1 mg per ml borate buffer, pH 8.4) were added to peripheral wells. A. Precipitin lines formed only with TDI-GSA and p-TMI-GSA. B. Antiserum reacted with each hapten-conjugate. No reaction occurred with GSA. C. Spur formation visible between reactions of antiserum with TDI-GSA and p-TMI-GSA.